United States Patent
Phillips, III et al.

(10) Patent No.: US 6,362,226 B2
(45) Date of Patent: Mar. 26, 2002

(54) MODULATION OF IN VIVO GLUTAMINE AND GLYCINE LEVELS IN THE TREATMENT OF AUTISM

(75) Inventors: John A. Phillips, III, Brentwood; Susan G. McGrew, Nashville, both of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/729,881

(22) Filed: Dec. 5, 2000

Related U.S. Application Data

(60) Provisional application No. 60/169,633, filed on Dec. 8, 1999.

(51) Int. Cl.[7] .................. A61K 31/19; A61K 31/44
(52) U.S. Cl. ................ 514/568; 514/570; 514/289
(58) Field of Search ................ 514/568, 570, 514/289

(56) References Cited

U.S. PATENT DOCUMENTS

| | | |
|---|---|---|
| 4,994,467 A | 2/1991 | Zimmerman |
| 5,008,251 A | 4/1991 | Gruber |
| 5,385,947 A | 1/1995 | Godel et al. |
| 5,474,990 A | 12/1995 | Olney |
| 5,506,231 A | 4/1996 | Lipton |
| 5,576,323 A | 11/1996 | Heinz et al. |
| 5,605,911 A | 2/1997 | Olney et al. |
| 5,866,585 A | 2/1999 | Fogel |
| 5,902,815 A | 5/1999 | Onley et al. |

OTHER PUBLICATIONS

Brusilow, "Phenylacetylglutamine May Replace Urea as a Vehicle for Waste Nitrogen Excretion," Pediatr. Res., vol. 29 (No. 2), p. 147–50, (1991). (Abstract only).

Carlsson, "Hypothesis: is Infantile Autism a Hypoglutamatergic Disorder? Relevance of Glutamate—Serotonin Interactions for Pharmacotherapy," J. Neurol. Transm., vol. 105 (No. 4–5), p. 525–535, (1998). (Abstract only).

Carlsson et al., "The 5–HT2A Receptor Antagonist M10097 is More Effective in Counteracting NMDA Antagonist–Than Dopamine Agonist–Induced Hyperactivity in Mice," J. Neurol. Transm., vol. 106 (No. 2), p. 123–129, (1999). (Abstract only).

Darmaun et al., "Phenylbutyrate–Induced Glutamine Depletion in Humans: Effect on Leucine Metabolism," Am. J. Physiol., vol. 274 (No. 5), p. E801–E807, (1998). (Abstract only).

Deutsch et al., "Glycine: a Possible Role in Lithium's Action and Affective Illness," Neuropsychobiology, vol. 9 (No. 4), p. 215–218, (1983). (Abstract only).

Hamberger et al., "Elevated CSF Glutamate in Rett Syndrome," Neuropediatrics, vol. 23 (No. 4), p. 212–213, (1992). (Abstract only).

Hashimoto et al., "Differenced in Brain Metabolites Between Patients with Autism and Mental Retardation as Detection by in vivo Localized Proton Magnetic Resonance Spectroscopy," J. Child. Neurol., vol. 12 (No. 2), p. 91–96, (1997). (Abstract only).

Khan et al., "Xeroderma Pigmentosum Group C Splice Mutation Associated with Autism and Hypoglycinemia," J. Invest. Dermatol., vol. 111 (No. 5), p. 791–796, (1998). (Abstract only).

Margolis et al., "cDNAs with Long CAG Trinucleotide Repeats from Human Brain," Hum. Genet., vol. 100 (No. 1), p. 114–122, (1997). (Abstract only).

McDougle et al., "Effects of Tryptophan Depletion in Drug–Free Adults with Autistic Disorder," Arch. Gen. Psychiatry, vol. 53 (No. 11), p. 993–1000, (1996). (Abstract only).

Moreno–Fuenmayor et al., "Plasma Excitatory Amino Acids in Autism," Invest. Clin., vol. 37 (No. 2), p. 113–128, (1996). (Abstract only).

Piscitelli et al., "Disposition of Phenylbutyrate and its Metabolites, Phenylacetate and Phenylacetylglutamine," J. Clin. Pharmacol., vol. 35 (No. 4), p. 368–373, (1995). (Abstract only).

Plecko et al., "Partial N–Acetylglutamate Synthetase Deficiency in a 13–Year–Old Girl: Diagnosis and Response to Treatment with N–Carbamylglutamate," Eur. J. Pediatr., vol. 157 (No. 12), p. 996–998, (1998). (Abstract only).

Warren et al., "Immunogenetic Studies in Autism and Related Disorders," Mol. Chem. Neuropathol., vol. 28 (No. 1–3), p. 77–81, (1996). (Abstract only).

*Primary Examiner*—William R. A. Jarvis
(74) *Attorney, Agent, or Firm*—Jenkins & Wilson, P.A.

(57) ABSTRACT

A method of treating autism in a patient. The method includes administering to the patient an effective amount of a glutamine level reducing agent, a glycine level reducing agent or combinations thereof. Representative glutamine level reducing agents are phenylbutyrate and phenylacetate, and a representative glycine level reducing agent is sodium benzoate. Optionally, an N-methyl-D-aspartate receptor antagonist can also be administered to the patient. A representative N-methyl-D-aspartate receptor antagonist is dextromethorphan.

35 Claims, No Drawings

MODULATION OF IN VIVO GLUTAMINE AND GLYCINE LEVELS IN THE TREATMENT OF AUTISM

CROSS REFERENCE TO RELATED APPLICATIONS

This application is based on and claims priority to U.S. provisional patent application serial No. 60/169,633, filed Dec. 8, 1999, herein incorporated by reference in its entirety.

TECHNICAL FIELD

The present invention relates to a method for treating autism in patients. More particularly, the present invention relates to a method for modulating in vivo levels of glutamine, glycine or both glutamine or glycine in the treatment of autism.

TABLE OF ABBREVIATIONS

| | |
|---|---|
| AICA | 5-amino-4-imidazolecarboxamide |
| BID | twice a day |
| CSF | cerebrospinal fluid |
| DM | dextromethorphan |
| EAA | excitatory amino acid |
| g | gram(s) |
| GABA | gamma-aminobutyric acid |
| Gln | glutamine |
| Glu | glutamate |
| Gly | glycine |
| kg | kilogram(s) |
| mg | milligram(s) |
| µmol/L | micromole per liter |
| NMDA | N-methyl-D-aspartate |
| PA | phenylacetate |
| PB | phenylbutyrate |
| PCP | phencyclidine |
| po | by mouth |
| SB | sodium benzoate |
| wk(s) | week(s) |

BACKGROUND OF THE INVENTION

Autism is a developmental disorder characterized by social relating and communicating impairments along with restricted, repetitive or stereotypical behavior and onset by three years of age. A genetic basis for the disorder is suggested by observations such as developmental anomalies in autistic patients, increased incidence of autism in siblings of autistic patients, and a tendency for both of a set of monozygotic twins to be either autistic or not autistic (also called "concordance" for a disorder). However, in 75–80% of autistic individuals, no underlying cause is found for the autism. Previous studies have implicated abnormalities involving neurotransmitters including serotonin, norepinephrine, and histamine in some cases of autism.

U.S. Pat. No. 4,994,467 issued Feb. 19, 1991 to Zimmerman discloses a method for treating autism in children by administration of therapeutically effective amounts of a N-methyl-D-aspartate (NMDA) receptor antagonist selected from the group consisting of ketamine and dextromethorphan.

U.S. Pat. No. 5,008,251 issued Apr. 16, 1991 to Gruber (assignee—Regents of the University of California) discloses methods for treatment of autism comprising administration of the compounds including the purine nucleoside 5-amino-4-imidazolecarboxamide riboside (AICA riboside), AICA ribotide, ribavirin, and ribavirin monophosphate.

U.S. Pat. No. 5,866,585 issued Feb. 2, 1999 to Fogel (assignee—Synchroneuron) discloses a method for treating tardive dyskinesia using the NMDA receptor antagonists dextromethorphan and memantine.

U.S. Pat. No. 5,506,231 issued Apr. 9, 1996 to Lipton (assignee—The Children's Medical Center Corporation) discloses the treatment of damage to the central nervous system in a patient resulting from infection with HIV with an NMDA receptor antagonist, such as dextromethorphan.

U.S. Pat. No. 5,605,911 issued Feb. 25, 1997 to Olney et al., (assignee—Washington University) discloses methods of treating or preventing central nervous system effects resulting from NMDA receptor hypofunction, including schizophrenia. The methods comprise administration to a patient in need thereof of an NMDA antagonist along with an alpha-2 adrenergic receptor agonist; or alternatively, the administration of an alpha-2 adrenergic receptor agonist drug alone.

U.S. Pat. No. 5,576,323 issued Nov. 19, 1996 to Heinz et al. (assignee—Eli Lilly and Company) discloses compounds that affect excitatory amino acid receptors, including the NMDA receptor, and that may be useful in the treatment of neurological disorders.

Despite the disclosure of the foregoing U.S. patents, there remains significant room for improvement in the treatment of autism, particularly in children. A treatment approach that is based on observed biochemical abnormalities in autistic patients would be desirable in view of the potential applicability of such an approach to the 75 to 80% of autistic individuals having primary autism in which no underlying cause is found. Such an approach is not currently available in the art.

SUMMARY OF THE INVENTION

A method of treating autism in a patient is disclosed. The method comprises administering to the patient an effective amount of a glutamine level reducing agent, a glycine level reducing agent or combinations of these with or without a modulator of the Gly NMDA receptor.

Accordingly, it is an object of this invention to provide an improved method of treating autism, particularly in children.

It is another object of this invention to provide a method of treating autism that is based on observed biochemical abnormalities in autistic patients.

It is a further object of this invention to provide a method of treating autism that is based on observed elevated levels of glutamine and glycine in autistic patients.

It is still a further object of this invention to provide a method of treating autism that pertains to the modulation of glutamine and glycine levels in autistic patients.

Some of the objects of the invention having been stated hereinabove, other objects will become evident as the description proceeds, when taken in connection with the accompanying Examples as best described hereinbelow.

DETAILED DESCRIPTION OF THE INVENTION

Autism is characterized by deficits in sociability, reciprocal verbal and nonverbal communication, repetitive or stereotypical behavior, and onset by 3 years of age. Most (i.e. about 75–80%) autistic individuals have primary autism in which no underlying cause is found.

In screening a series of consecutive autistic probands, the present co-inventors detected 5/36 (14%) who had elevated plasma levels of glutamine (Gln) or glycine (Gly), or elevated levels of both Gln and Gly, on repeated studies. One patient in the screening series was diagnosed as having autism at age 2 years, 10 months. His Gln (mean 884 µmol/L—normal 370–682 µmol/L) and Gly (mean 379 µmol/L—normal 120–315 µmol/L) levels were consistently elevated above the normal range on all 5 studies done between age 4 years, 1 1 months and age 6. Urine Gln and Gly levels were 1410 µmol/g creatinine (normal 165–510 µmol/g creatinine) and 5663 µmol/g creatinine (normal 569–1395 µmol/g creatinine), respectively. His cerebrospinal fluid (CSF) Gln was 708 µmol/L (normal 356–680 µmol/L) while his CSF Gly level was normal. His electrolytes, anion gap and plasma ammonia levels were all well within the normal range and his urine organic acid profile was normal. Another patient in the series had persistent elevated Gly levels on multiple plasma amino acid profiles. These levels ranged from 324–439 µmol/L (normal for age ranges from 120–315 µmol/L).

The present invention thus pertains to the identification of elevated levels of glutamine and glycine as compared to normal levels in autistic patients, and particularly in autistic children. The present invention thus also pertains to a method of treating autism in a patient comprising administering to the patient an effective amount of a glutamine level reducing agent (e.g. phenylbutyrate or PB), a glycine level reducing agent (e.g. sodium benzoate or SB) or combinations of these agents, with or without a modulator of the Gly NMDA receptor (e.g. dextromethorphan or DM). Until the disclosure of the present invention, a role for modulation of in vivo glutamine and glycine levels in the treatment of autism has not been characterized in the art. Correspondingly, prior to the disclosure of the present invention, no motivation can be found in the art to modulate in vivo glutamine and glycine levels in the treatment of autism.

A. General Considerations

Glutamic acid is one of the 20 common amino acids used by all living cells to make protein. The ionized form of glutamic acid, glutamate, is the predominant form of this compound in neutral solutions. In mammals, glutamate serves as the predominant excitatory neurotransmitter in mammalian central nervous systems. See e.g., Olney. J. W., "Glutamate," pp. 468–70 in *Encyclopedia of Neuroscience*, G. Adelman, ed. (Birkhauser, Boston, 1987). Glutamate (Glu) is also employed in vivo as a precursor in the production of glutamine (Gln), also one of the 20 common amino acids used by all living cells to make protein. As is well known in the art, glutamate and glutamine are structurally very similar, varying only in the presence of an amino group (Gln) instead of a carboxyl group (Glu) on the side chain of each amino acid.

Glutamate exerts its effects on glutamate receptors found on neurons. When the glutamate receptor is activated by glutamate, it changes conformation and alters ion channels that consequently change the chemical ionic gradient across the neuron cell membrane. This mechanism is a basis for nerve signals. Since glutamate is an amino acid that serves as an excitatory neurotransmitter inside the brain, it is often called an "excitatory amino acid" (EM). Glutamate receptors may also be activated by another amino acid, aspartate, and hence glutamate receptors are also called "EAA receptors". However, glutamate is utilized much more than aspartate as a neurotransmitter, and EAA receptors are more typically referred to as "glutamate receptors". The N-methyl-D-aspartate (NMDA) receptor is an example of an EAA receptor.

Phenylbutyrate (PB) conjugates to glutamine in vivo and has been used in the art to treat urea cycle disorders. It has thus been reported that phenylbutyrate treatment can decrease plasma glutamine levels. See Darmaun et al., *Am. J. Physiol.* 274: E801–07 (1998). It has also been reported that phenylbutyrate is rapidly converted in vivo to phenylacetate by first pass liver metabolism. See Piscitelli et al., *J. Clin. Pharmacol.* 35:368–73 (1995). It has further been reported that phenylacetylglutamine, the amino acid acetylation product of phenylacetate, serves as a waste nitrogen product, and the formation of phenylacetylglutamine reduces glutamine levels. See Brusilow, *Pediatr. Res.* 29: 147–50 (1991). While it is not the desire of the present co-inventors to be bound by an particular method of action, the lowering of glutamine is contemplated to decrease the stimulation of the EAA receptors that is contemplated to occur in autistic patients with high levels of glutamine.

Glycine has a regulatory binding site on NMDA-type EAA receptors on neurons. Glutamate is the primary neurotransmitter, while glycine plays a co-agonist role. Sodium benzoate is a well known and widely used preservative for pharmaceutical products such as syrups, flavored vehicles, and multiple dose containers for liquid preparations. Sodium benzoate is also used as a diagnostic acid for liver function and as a glycine level reducing agent. Sodium benzoate is thus contemplated to be useful in the treatment of the autistic patients with elevated glutamine or glycine, or both, when administered alone or in conjunction with a glutamine level reducing agent (e.g. phenylbutyrate and phenylacetate) in accordance with the present invention.

Dextromethorphan has as one of its properties the ability to retard glycine binding to an NMDA-type EAA receptor. Hence, dextromethorphan is contemplated to be useful in the treatment of the autistic patients with elevated glutamine or glycine, or both, when administered in conjunction with a glutamine level reducing agent (e.g. phenylbutyrate and phenylacetate) and/or a glycine level reducing agent (e.g. sodium benzoate) in accordance with the present invention.

B. Definitions

The terms "elevated glutamine level" or "elevated glycine level" are meant to refer to in vivo glutamine or glycine levels that are elevated to any extent over normal ranges of in vivo glutamine levels. Representative normal ranges of glutamine and glycine are disclosed herein. Glutamine and glycine levels are measured in any suitable biological sample from a patient, including, but not limited to, a blood or plasma sample, an urine sample or a cerebrospinal fluid (CSF) sample. In view of the fact that the glutamine and glycine levels described herein in accordance with the present invention are elevated above normal ranges, the elevated glutamine and elevated glycine levels are also referred to herein as "abnormal" or as an "abnormality".

The term "a glutamine level reducing agent" is meant to refer to an agent which acts to reduce in vivo glutamine levels in a subject after the agent is administered to the subject. Glutamine levels are measured in any suitable biological sample from a patient, including, but not limited to, a blood or plasma sample, an urine sample or a CSF sample. Preferred examples of glutamine level reducing agents are phenylacetate and phenylbutyrate, although any pharmaceutically acceptable agent which acts to reduce glutamine levels is contemplated in accordance with the present invention.

Phenylacetate is metabolized to phenylbutyrate in first pass liver metabolism and is a more preferred embodiment of the agent because it is more palatable in an oral form. Phenylacetate and phenylbutyrate are commercially available from Medicis Pharmaceutical Corporation, Phoenix, Ariz.

The term "glycine level-reducing agent" is meant to refer to an agent which, upon administration to a subject, acts to reduce in vivo glycine levels in the subject. Glycine levels are measured in any suitable biological sample from a patient, including, but not limited to, a blood or plasma sample, an urine sample or a CSF sample. Sodium benzoate is a representative glycine level reducing agent, although any pharmaceutically acceptable agent which acts to reduce glutamine levels is contemplated in accordance with the present invention. Sodium benzoate is commercially available from Medicis Pharmaceutical Corporation, Phoenix, Ariz.

As used herein, an "effective" dose refers to one that is administered in doses tailored to each individual patient manifesting symptoms of autism sufficient to cause an improvement in the patients' expressive and receptive language skills, attention span and focus, motor planning and/or socialization with peers, with tolerable adverse effects. Representative dosage ranges for glutamine level reducing agents and glycine level reducing agents are disclosed herein. Further, after review of the disclosure of the present invention presented herein, one of ordinary skill in the art can tailor the dosages to an individual patient, taking into account the particular formulation and method of administration to be used with the compound as well as patient height, weight, severity of symptoms, and stage of the disorder to be treated.

An effective dose and a therapeutically effective dose are generally synonymous. However, compounds may be administered to patients having reduced symptoms or even administered to patients as a preventative measure. Hence, the compound may be effective in therapeutic treatment even in the absence of symptoms of the disorder.

A "receptor" is a macromolecular binding site which is at least partially exposed on the surface of a cell, and has specific and limited affinity for one or more molecules called "ligands", which are typically neurotransmitters or hormones in their natural and native setting in vivo and may be drugs or other compounds, whether natural or synthetic in origin. When a ligand contacts an appropriate receptor, a brief binding reaction occurs which evokes a response, such as activation and depolarization of a neuron. Most receptor molecules are proteins which straddle the membrane of a cell, with an external portion for binding reactions and an internal portion which contributes to the cellular response to ligand binding. The term "receptor" may include various additional components, such as an ion channel associated with a receptor, perhaps merely by proximity, which is affected by the receptor.

An "agonist" is a molecule which activates a certain type of receptor. For example, glutamate molecules act as agonists when they excite EM receptors. By contrast, an "antagonist" is a molecule which prevents or reduces the effects exerted by an agonist on a receptor. Many naturally-occurring neurotransmitters are agonists, since they activate the receptors they interact with. By contrast, artificial and/or exogenous drugs may be agonists or antagonists. For example, NMDA antagonists are drugs that can suppress excitatory activity of glutamate or glycine at NMDA receptors.

Although agonist and antagonist compounds are generally thought to interact directly with receptors to achieve their effects, such effectivity may not result from direct interaction but may involve intermediate steps or compounds. Hence, the present invention is not limited to mechanisms acting directly on affected receptors involved or thought to be involved in autistic disorders. Rather, any effect of the compounds on receptors or more generally on metabolism or symptoms of the disorder is contemplated as part of the present invention. It is further noted that both Glu and Gly are non-essential amino acids. Thus, dietary restriction of Glu and/or Gly is not preferred in lowering Glu and/or Gly levels.

C. Therapeutic Methods

In accordance with the present invention a method for treating autism is provided. The method comprises administrating a pharmaceutical composition containing an effective amount of an agent that acts to reduce glutamine levels and/or an agent that acts to reduce glycine levels in a patient, particularly a human patient, for the treatment of autism or another pervasive developmental disorder (e.g. tardive dyskinesia).

In a preferred embodiment, the autistic patient has increased levels of glutamine, increased levels of glycine or increased levels of both glutamine and glycine. Glutamine and glycine level are measured in any suitable biological sample from a patient, including, but not limited to, a blood or plasma sample, an urine sample or a CSF sample.

Glutamine level reducing agents and glycine level reducing agents (e.g. phenylbutyrate, phenylacetate, sodium benzoate) are preferably administered in amounts ranging from about 10 mg/kg body weight/day to about 1000 mg/kg body weight/day, more preferably from about 50 mg/kg body weight/day to about 800 mg/kg body weight/day, and even more preferably in amounts ranging from about 250 to about 500 mg/kg body weight/day. The use of at least about 100, 200, 300, 400 and/or 500 mg/kg body weight/day of a glutamine level reducing agent or glycine level reducing agent is further contemplated.

These dosages can be administered when the glutamine level reducing agents and glycine level reducing agents are administered alone or when the glutamine level reducing agents and glycine level reducing agents are administered together. However, in a preferred embodiment, a glutamine level reducing agent and a glycine level reducing agent are administered in lower amounts when administered together as compared to dosage amounts when the glutamine level reducing agent and the glycine level reducing agent are administered alone.

The unit dose can be administered, for example, 1 to 4 times per day. Most preferably, the unit dose is administered twice a day (BID). The dose depends on the route of administration and the formulation of a composition containing the compound or compounds. Further, it will be appreciated by one of ordinary skill in the art after receiving the disclosure of the present invention that it may be necessary to make routine adjustments or variations to the dosage depending on the combination of agents employed, on the age and weight of the patient, and on the severity of the condition to be treated.

Such adjustments or variations, as well as evaluation of when and how to make such adjustments or variations, are well known to those of ordinary skill in the art of medicine. Evaluation parameters and techniques may vary with the patient and the severity of the disease. Particularly useful evaluative techniques for autism include assessment of expressive and receptive language skills, attention span and focus, motor planning and socialization with peers.

Further, the methods of the present invention are envisioned to be beneficial in combination with certain other treatments. Such other treatments are anticipated to be those enhancing the efficacy of the present invention by acting via a similar mechanism. Additionally, such treatments may act by a different mechanism than the methods of the present invention but enhance its efficacy either in the treatment of autism or other diseases or disorders in autistic patients.

For example, the methods of the present invention can further comprise administering an NMDA receptor antagonist to the autistic patient. A representative NMDA receptor antagonist is dextromethorphan, although any pharmaceutically acceptable agent which acts as an NMDA receptor antagonist is contemplated in accordance with the present invention.

The NMDA receptor antagonist can be administered in dosages ranging from about 0.1 mg/kg body weight/day to about 10 mg/kg body weight/day, preferably from about 1–1.5 mg/kg body weight/day to about 8 mg/kg body weight/day, and more preferably in amounts ranging from about 2.5 to about 5 mg/kg body weight/day. Dosages of at least about 1, 2, 3, 4 and/or 5 mg/kg body weight/day of a NMDA receptor antagonist can also be administered.

The co-administration of a glutamine level reducing agent and a glycine level reducing agent, a glutamine level reducing agent and an NMDA receptor antagonist, a glycine level reducing agent and an NMDA receptor antagonist, or a glutamine level reducing agent, a glycine level reducing agent and an NMDA receptor antagonist in accordance with the present invention is contemplated to produce additional synergistic therapeutic effects in the autistic patient. Thus, the methods of the present invention represent a significant improvement in the treatment of autism, particularly in children.

Indeed, the methods of the present invention are based on observed biochemical abnormalities, i.e. elevated glutamine and glycine levels. As such, the methods of the present invention are contemplated to be applicable to the 75 to 80% of autistic individuals having primary autism in which no underlying cause is found.

D. Pharmaceutical Compositions

Pharmaceutical compositions for use in accordance with the present invention may be formulated in conventional manner using one or more physiologically acceptable carriers or excipients. Thus, the compounds for use according to the present invention may be formulated for oral, buccal, parenteral, rectal or transdermal administration or in a form suitable for administration by inhalation or insufflation (either through the mouth or the nose). Administration may also be accomplished by any other effective means.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the compositions may take the form of tablets or lozenges formulated in conventional manner.

The methods of administration according to the present invention may include parenteral administration by injection, for example by bolus injection or continuous infusion. Formulations for injection may be presented in unit dosage form, e.g., in ampules or in multi-dose containers, with or without an added preservative. The compositions used in the methods may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use. The compounds may also be formulated in rectal compositions such as suppositories or retention enemas, e.g. containing conventional suppository bases such as cocoa butter or other glycerides. In addition to the formulations described previously, the compounds may also be formulated as a preparation for implantation or injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Administration of Dextromethorphan to Children with Autism Having Increased Plasma Levels of Glutamine, Glycine or Both Glutamine and Glycine Autistic patients were screened for elevated plasma levels of glutamine or glycine, or both. Five of 36 patients had elevated levels of either or both amino acids. One patient, "B", had been diagnosed as having autism at age 2 years and 10 months. Normal glutamine levels range from measurements of 370 to 682 $\mu$mol/L; B's levels were consistently elevated and had a mean of 884 $\mu$mol/L. Similarly, normal glycine levels range from measurements of 120 to 315 $\mu$mol/L; B's levels were consistently elevated and had a mean of 379 $\mu$mol/L. Urine measurements of glutamine was 1410 $\mu$mol/g creatinine, where normal range is 165–510 $\mu$mol/g creatinine; urine measurements of glycine was 5663 $\mu$mol/g creatinine, where normal range is from 569 to 1395 $\mu$mol/g creatinine. Further, B had elevated levels of glutamine in his cerebrospinal fluid, although his glycine levels were within the normal range. His routine chemistry lab tests, including his urine organic acid profile, were normal. Patient "F" had persistent elevated glycine levels on multiple amino acid profiles which ranged from 324 to 439 $\mu$mol/L, where normal levels are from 120 to 315 $\mu$mol/L.

Both patients B and F were treated with dextromethorphan at 5 mg/kg body weight/day in the form of a cough and cold preparation sold under the registered trademark DELSYM® by McNeilLab, Inc. of Spring House, Pa., divided BID. Both patients' special education and classroom teachers and speech and occupational therapists, who were blinded to treatment, reported significant improvement in the patients' expressive and receptive language skills, attention span and focus, motor planning and socialization with peers.

After withdrawal of dextromethorphan treatment, all of the treatment-blinded observers noted regression in all of these areas of behavior measurement which had previously shown improvement. Upon resumption of long-term dextromethorphan treatment, the patients responded as before and have continued to respond to the treatment.

Example 2

Treatment of Autistic Patients with Phenylbutyrate and/or Sodium Benzoate Alone, Together or in Combination with Dextromethorphan in Single-Blinded Placebo Controlled Study In accordance with the present invention, this Example employs a single center, single blind, placebo controlled design to compare effectiveness of Phenylbutyrate (PB), Sodium Benzoate (SB), combinations of PB and SB, and combinations of PB, SB and dextromethorphan (DM) in the treatment of children with autism and either normal or increased plasma levels of glycine and/or glutamine. A sample of twelve children with autism is used, with five months' participation for each child and with 12 months' duration for the study. Six of the patients in the sample have normal plasma and urinary amino acid levels, three have increased plasma and urinary amino acid levels of glutamine, and three have increased plasma and urinary amino acid levels of glycine and glutamine.

Subjects are selected from a cohort of autistic patients followed by co-inventor Dr. Susan McGrew. They are classified as having normal plasma amino acid levels, increased plasma levels of glycine or glutamine, or increased levels of both glycine and glutamine based on their amino acid levels. PB and SB are given at doses ranging from 250 to 500 mg/kg body weight/day po. DM is given at doses ranging from 2.5 to 5 mg/kg body weight/day po. Matching placebo for each medication is also administered po.

Language samples are observed during a 30 minute audio/video tape which is then scored per protocol disclosed below by a speech pathologist. Data is entered by a psychology graduate student. Attention assessment is evaluated by the Leiter-R test and Digit Span from the Children's Memory Scale and administered by a psychologist. Social and Behavioral Assessments are done using the Nisonger Child Behavior Questionnaire for Autism and Dr. Stone's Behavior Questionnaire for Autism. These are completed by parents and teachers, then scored and entered by a psychology graduate student. The CARS (Childhood Autism Rating Scale) is administered by a psychologist. In all cases the rater is blinded to the treatment protocol. Plasma and urinary levels of amino acids are also evaluated as secondary parameters.

Example 1 discloses that 5/36 (14%) of children with autism have increased plasma levels of glutamine, glycine or both glutamine and glycine. In Example 1, an autistic patient with elevated glutamine and glycine and an autistic patient with glycine were treated with DM at 5 mg/kg body weight/day. A clinical improvement in their autistic behavior was observed. The procedures of Example 1, however, were uncontrolled and open-label. In Example 2, treatment of children with autism with PB, SB or combinations of PB, SB and DM is systematically evaluated.

Subject Population

Inclusion Criteria: Subjects are classified as having normal plasma amino acid levels, increased plasma levels of glycine or glutamine, or both increased plasma glutamine and glycine based on their plasma amino acid levels. Those with elevations are confirmed on three independent amino acid studies to have consistent elevations.

Exclusion Criteria: Subjects having an identified genetic disorder such as Fragile X syndrome, homocystinuria or organic acidemia are excluded from the study.

Medications. PB and SB are administered orally in a liquid form at 250 then 500 mg/kg body weight/day, divided BID, when administered alone or in combination with each other or with DM. DM is administered orally in a liquid form at 2.5 then 5 mg/kg body weight/day when administered in combination with PB, SB, or both PB and SB.

Screening Procedure. Children who meet inclusion and exclusion criteria are screened after obtaining written informed consent approved by the Vanderbilt University Institutional Review Board. Screening comprises a medical history and physical examination. Fasting blood is obtained for routine hematology and clinical chemistry.

General Study Design. The order of the interventions is: (1) baseline measurements followed by a run-in placebo period and repeated measurements; (2) treatment period 1, patients randomized to either PB or SB, (3) treatment period 11, addition of either SB or PB; (4) addition of DM to the combination of PB+SB; and (5) second placebo period, recovery.

Thus, this Example adopts a fixed sequence of treatment or study periods, as follows:

Study Periods

Placebo-Baseline or run in: Baseline data is collected and patients are then given placebo and become familiar to the study protocol. Patients receive matching placebos of each of the three active medications. Unallowed medications are withdrawn prior to this period. At the end of the period, the baseline data is collected to assess any potential "placebo effect".

Active treatment period I: Patients are randomized to receive either PB or SB. This portion of the study is double blind, and the patients receive the other medication.

Active treatment period II: The active medication not received in treatment period I is added.

Active treatment period III: DM is added to the combination of PB+SB.

Washout period: Active medications are replaced for placebos to determine if a deterioration in functional status is apparent after withdrawal of active medication.

Each treatment period lasts 4 weeks. This is envisioned as the minimum time required to ensure that steady state conditions are reached during active treatment, and that effective medication withdrawal is reached during washout periods. At the end of each treatment period, the following measurements are taken: behavioral assessment, plasma and urinary amino acid levels. Behavioral assessments are prepared as described above. The interviewer/examiner is blinded to the treatment received.

Statistical Considerations: Half of the patients receive first PB only, and the other half receive SB only. Comparison between PB and SB, therefore, can be performed by un-pair analysis. Paired analysis can be performed between the treatment groups.

The respective doses of PB, SB and DM are escalated in two steps during each study period (250 then 500 mg/kg body weight/day for PB and SB; 2.5 then 5 mg/kg body weight/day for DM) and the same is done with the placebo. The study periods are summarized in Table 1 below.

TABLE 1

Study Periods

| Testing | Baseline - Placebos | PB or SB 4 wks | PB + SB 4 wks | PB + SB + DM 4 wks | Placebos 4 wks |
|---|---|---|---|---|---|
| Behavior | X | X | X | X | X |
|  | X |  |  |  |  |
| Plasma AA | X | X | X | X | X |
| Urine OA | X |  |  |  |  |

Given that treatment periods have a fixed sequence, investigators are not be blinded to the treatment period. However, both the patient and the behavioral assessor are blinded to this treatment scheme. Given that behavioral assessment is the main endpoint, this can be considered a double-blind study design.

Ethical considerations: Assent is obtained from the patients, and signed written consent is obtained from the parent or legal guardian. Both the patient and the guardian are blinded to the treatment received. They are informed that the patient receives placebo during one or more treatment periods, but are not told when.

REFERENCES

The references listed below as well as all references cited in the specification are incorporated herein by reference to the extent that they supplement, explain, provide a background for or teach methodology, techniques and/or compositions employed herein.

Brusilow, *Pediatr. Res.* 29:147–50 (1991).
Darmaun et al., *Am. J. Physiol.* 274: E801–07 (1998).
Olney, J. W., "Glutamate," pp. 468–70 in *Encyclopedia of Neuroscience*, G. Adelman, ed. (Birkhauser, Boston, 1987).
Piscitelli et al., *J. Clin. Pharmacol.* 35:368–73 (1995).
U.S. Pat. No. 4,994,467
U.S. Pat. No. 5,008,251
U.S. Pat. No. 5,506,231
U.S. Pat. No. 5,576,323
U.S. Pat. No. 5,605,911
U.S. Pat. No. 5,866,585
U.S. Pat. No. 5,902,815

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of treating autism in a patient comprising administering to the patient an effective amount of a glutamine level reducing agent, a glycine level reducing agent or combinations thereof.

2. The method of claim 1, wherein the patient has elevated levels of glutamine.

3. The method of claim 1, wherein the patient has elevated levels of glycine.

4. The method of claim 1, wherein the patient has elevated levels of both glutamine and glycine.

5. The method of claim 1, wherein the glutamine level reducing agent, the glycine level reducing agent, or both the glutamine level reducing agent and the glycine level reducing agent are administered in a dose ranging from about 10 to about 1000 mg/kg body weight/day.

6. The method of claim 5, wherein the glutamine level reducing agent, the glycine level reducing agent, or both the glutamine level reducing agent and the glycine level reducing agent are administered in a dose ranging from about 50 to about 800 mg/kg body weight/day.

7. The method of claim 6, wherein the glutamine level reducing agent, the glycine level reducing agent, or both the glutamine level reducing agent and the glycine level reducing agent are administered in a dose ranging from about 250 to about 500 mg/kg body weight/day.

8. The method of claim 1, wherein the glutamine level reducing agent comprises phenylbutyrate or phenylacetate.

9. The method of claim 1, wherein the glycine level reducing agent comprises sodium benzoate.

10. The method of claim 1, further comprising administering an N-methyl-D-aspartate receptor antagonist to the patient.

11. The method of claim 10, wherein the N-methyl-D-aspartate receptor antagonist is administered in a dose ranging from about 0.1 to about 10 mg/kg body weight/day.

12. The method of claim 11, wherein the N-methyl-D-aspartate receptor antagonist is administered in a dose ranging from about 1 to about 8 mg/kg body weight/day.

13. The method of claim 12, wherein the N-methyl-D-aspartate receptor antagonist is administered in a dose ranging from about 2.5 to about 5 mg/kg body weight/day.

14. The method of claim 10, wherein the N-methyl-D-aspartate receptor antagonist is dextromethorphan.

15. A method of treating autism in a patient having increased levels of glutamine, increased levels of glycine or increased levels of both glutamine and glycine, the method comprising administering to the patient an effective amount of a glutamine level reducing agent, a glycine level reducing agent or combinations thereof.

16. The method of claim 15, wherein the glutamine level reducing agent, the glycine level reducing agent, or both the glutamine level reducing agent and the glycine level reducing agent are administered in a dose ranging from about 10 to about 1000 mg/kg body weight/day.

17. The method of claim 16, wherein the glutamine level reducing agent, the glycine level reducing agent, or both the glutamine level reducing agent and the glycine level reducing agent are administered in a dose ranging from about 50 to about 800 mg/kg body weight/day.

18. The method of claim 17, wherein the glutamine level reducing agent, the glycine level reducing agent, or both the glutamine level reducing agent and the glycine level reducing agent are administered in a dose ranging from about 250 to about 500 mg/kg body weight/day.

19. The method of claim 15, wherein the glutamine level reducing agent comprises phenylbutyrate or phenylacetate.

20. The method of claim 15, wherein the glycine level reducing agent comprises sodium benzoate.

21. The method of claim 15, further comprising administering an N-methyl-D-aspartate receptor antagonist to the patient.

22. The method of claim 21, wherein the N-methyl-D-aspartate receptor antagonist is administered in a dose ranging from about 0.1 to about 10 mg/kg body weight/day.

23. The method of claim 22, wherein the N-methyl-D-aspartate receptor antagonist is administered in a dose ranging from about 1 to about 8 mg/kg body weight/day.

24. The method of claim 23, wherein the N-methyl-D-aspartate receptor antagonist is administered in a dose ranging from about 2.5 to about 5 mg/kg body weight/day.

25. The method of claim 21, wherein the N-methyl-D-aspartate receptor antagonist is dextromethorphan.

26. A method of treating autism in a patient having increased levels of glutamine, increased levels of glycine or increased levels of both glutamine and glycine, the method comprising co-administering to the patient an effective amount of a glutamine level reducing agent, a glycine level reducing agent or combinations thereof, and an effective amount of an N-methyl-D-aspartate receptor antagonist.

27. The method of claim 26, wherein the glutamine level reducing agent, the glycine level reducing agent, or both the glutamine level reducing agent and the glycine level reducing agent are administered in a dose ranging from about 10 to about 1000 mg/kg body weight/day.

28. The method of claim 27, wherein the glutamine level reducing agent, the glycine level reducing agent, or both the glutamine level reducing agent and the glycine level reducing agent are administered in a dose ranging from about 50 to about 800 mg/kg body weight/day.

29. The method of claim 28, wherein the glutamine level reducing agent, the glycine level reducing agent, or both the glutamine level reducing agent and the glycine level reducing agent are administered in a dose ranging from about 250 to about 500 mg/kg body weight/day.

30. The method of claim 26, wherein the N-methyl-D-aspartate receptor antagonist is administered in a dose ranging from about 0.1 to about 10 mg/kg body weight/day.

31. The method of claim 30, wherein the N-methyl-D-aspartate receptor antagonist is administered in a dose ranging from about 1 to about 8 mg/kg body weight/day.

32. The method of claim 31, wherein the N-methyl-D-aspartate receptor antagonist is administered in a dose ranging from about 2.5 to about 5 mg/kg body weight/day.

33. The method of claim 26, wherein the glutamine level reducing agent comprises phenylbutyrate or phenylacetate.

34. The method of claim 26, wherein the glycine level reducing agent comprises sodium benzoate.

35. The method of claim 26, wherein the N-methyl-D-aspartate receptor antagonist comprises dextromethorphan.

* * * * *